US012427269B2

(12) United States Patent
Malviya et al.

(10) Patent No.: US 12,427,269 B2
(45) Date of Patent: Sep. 30, 2025

(54) BUTTON OPERATED SINGLE HAND OPENING PACKAGE

(71) Applicant: Becton, Dickinson and Company, Franklin Lakes, NJ (US)

(72) Inventors: Rahul Malviya, Karnataka (IN); Amarsinh Deeliprao Jadhav, Karnataka (IN); Hemant Vilas Belsare, Karnataka (IN); Kadamb Gupta, Uttar Pradesh (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 683 days.

(21) Appl. No.: 17/893,441

(22) Filed: Aug. 23, 2022

(65) Prior Publication Data
US 2023/0068501 A1 Mar. 2, 2023

Related U.S. Application Data

(60) Provisional application No. 63/239,481, filed on Sep. 1, 2021.

(51) Int. Cl.
*A61M 5/50* (2006.01)
*A61M 5/315* (2006.01)
*A61M 5/32* (2006.01)

(52) U.S. Cl.
CPC ........ *A61M 5/508* (2013.01); *A61M 5/31515* (2013.01); *A61M 5/3202* (2013.01); *A61M 5/3234* (2013.01)

(58) Field of Classification Search
CPC .............. A61M 5/508; A61M 5/31515; A61M 5/3202; A61M 5/3234; A61M 2205/58; A61M 5/002

USPC .......................................................... 206/364
See application file for complete search history.

(56) References Cited

U.S. PATENT DOCUMENTS

| | | | | |
|---|---|---|---|---|
| 3,101,841 A | * | 8/1963 | Baldwin | A61M 5/3202 206/459.1 |
| 3,149,717 A | * | 9/1964 | Castelli | A61M 5/3202 206/459.1 |
| 4,113,090 A | * | 9/1978 | Carstens | A61M 5/3202 206/571 |
| 4,610,667 A | * | 9/1986 | Pedicano | A61M 5/3213 604/263 |

(Continued)

FOREIGN PATENT DOCUMENTS

JP H11334757 A 12/1999

OTHER PUBLICATIONS

PCT International Search Report and Written Opinion in PCT/US2022/041297 dated Dec. 2, 2022, 14 pages.

*Primary Examiner* — Andrew D Perreault
(74) *Attorney, Agent, or Firm* — Servilla Whitney LLC

(57) ABSTRACT

A hard package assembly is disclosed having a cam mechanism for ejecting a syringe from a hard package container with the use of a single hand. The cam mechanism including a push button and a button retainer, the push button having a trapezoidal body having a button face, a distal face adjacent and distal to the button face and a sloped face opposite the button face, the button retainer having a proximal portion, a distal portion in contact with the sloped face of the push button and a distal hook in contact with a bottom surface of the barrel flange. A method of use and a method of assembly are also disclosed.

25 Claims, 9 Drawing Sheets

(56) References Cited

U.S. PATENT DOCUMENTS 7,268,359 B2 * 9/2007 Fu .......................... G21F 5/018
250/507.1
2014/0013718 A1 1/2014 Maasarani et al.

* cited by examiner

BUTTON OPERATED SINGLE HAND OPENING PACKAGE

CROSS-REFERENCE TO RELATED APPLICATIONS

This application claims priority under 35 U.S.C. § 119(e) to U.S. Provisional Application No. 63/239,481, filed Sep. 1, 2021, the disclosures of which are incorporated herein by reference in their entirety.

TECHNICAL FIELD

The present disclosure relates to a hard package for a syringe and cannula, and in particular a hard package for a syringe and cannula having a mechanism for single-hand opening and operation.

BACKGROUND

Clean or sterile articles particularly useful for medical applications are packaged to preserve their sterility. The packaging for these articles is intended to provide a barrier to prevent microorganisms from entering inside the packaging to contaminate its contents. In most instances, the packaging is opened immediately prior to using the article, so as to minimize the time period in which the article is exposed to unsterile conditions. After use of the needle, package is discarded separate from the needle.

Current practice for opening a conventional package storing a syringe and needle requires involvement of both the hands. However, this practice presents its own set of challenges during an emergency situation where there can also be either time constraints or spatial challenges, which may consequently result in increasing the time, complexity and needle-related injuries to practitioners or patients. By way of example, current practices utilize blister packaging or air-tight bags which require peeling or separation of materials by pulling two pieces of the device apart with both hands. Further examples include capsules or containers with weak points which can either be broken by the user or pierced by the item inside the package. Said conventional methods can require both hands to manipulate the package and can also require both hands to remove the item from the package as one hand has to hold the package while the other pulls the item out.

In some instances, where practitioners may have only one hand available to open packaging that was designed for two hands, practitioners in emergency situations may use trauma shears or their own teeth, which may cause contamination or delay treatment.

When a "conventional" hypodermic needle is retrieved from a conventional package, the needle cannula shield is removed and then the plastic hub is attached to a luer lock or luer slip syringe. Drug from a vial is then retrieved and administered to the patient via injection. The needle is then discarded either as is or after capping using a recommended method of capping. On the other hand, a safety needle has an extra step wherein an additional component, the safety shield, is deployed to permanently "engulf" the needle thereby making it inaccessible. This ensures that the needle cannot be reused but also adds material costs and complexity to the package. This extra step is enabled by either a unique hub design that acts as a base for the safety mechanism to attach onto or a very complicated safety shield mechanism. Such hubs may be bulkier and more difficult to mold compared to a conventional needle hub. Similarly, the safety mechanism itself is also composed of a component that is difficult to mold and is also bulky. Additionally, the needle shield that protects the needle pre-use provides no utility post use and is discarded adding to the plastic usage and waste.

Thus, there is a need for a single hand-operable package which provides easy, reliable and repeatable fast access to the product. There is a further need for a package in which a used needle and syringe can be placed within for easy disposal.

SUMMARY

One or more embodiments are directed to single-hand operable hard package assembly comprising a hard package container, a syringe, a cam mechanism and a seal which encloses the syringe and cam mechanism within the hard package container.

The hard package container comprises a main compartment and an ejection compartment, the ejection compartment having a rectangular cross-sectional shape with an opening having a distal edge positioned on a short face of the rectangular shape of the ejection compartment, the ejection compartment is further defined by an inside surface, an open end at a right angle and proximal to the short face and a bottom surface at a right angle and distal to the short face.

The syringe comprises a plunger rod and a barrel positioned at least partially within the main compartment, the plunger rod having a proximal end, the barrel having a barrel flange, the barrel flange having a bottom surface.

The cam mechanism comprises a push button and a button retainer, the push button having a trapezoidal body having a button face, a distal face adjacent and distal to the button face and a sloped face opposite the button face, the button retainer having a proximal portion, a distal portion in contact with the sloped face of the push button and a distal hook in contact with a bottom surface of the barrel flange.

The seal covers the top end and the button face of the hard package container and the cam mechanism.

In some embodiments, the syringe further comprising a needle hub and needle cannula, the needle hub and needle cannula stored without a needle cap or sleeve within a cannula compartment of the hard package container. In some embodiments, the main compartment and cannula compartment share a common central axis C.

In some embodiments, the main compartment has a central axis C and the ejection compartment is offset from the central axis C, and the short face extends a distance DS from the central axis C such that components of the cam mechanism can be positioned within the ejection compartment.

In some embodiments, the ejection compartment further comprises a rounded or oval face opposite the short face for conforming to a hand of a practitioner.

In some embodiments, the ejection compartment further comprises a retainer guide path adjacent to the opening and positioned on the inside surface of the ejection compartment, the retainer guide path configured to interdigitate with a guide tab of the button retainer. In some embodiments, the retainer guide path has of two protrusions extending from the inside surface of the ejection compartment.

In some embodiments, the button retainer further comprises guide tabs extending outwardly from the proximal portion, the guide tabs configured to interdigitate with retainer guide path adjacent to the opening and positioned on the inside surface of the ejection compartment, the guide tabs configured to allow pivoting of the distal portion relative to the proximal portion.

In some embodiments, the bottom surface of the ejection compartment further comprises a protrusion on which the distal face of the push button slides on, the protrusion adjacent to the opening and extends from the bottom surface in a proximal direction. In some embodiments, the protrusion does not extend beyond the distal edge of the opening such that the opening is unobstructed. In some embodiments, the protrusion further comprises a step which extends beyond the distal edge of the opening, the step configured to limit travel of the push button in a medial direction. In some embodiments, the push button further comprising a distal flange extending distally from the button face, the distal flange abutting the distal edge of the opening, the distal flange slidable along the protrusion of the bottom surface. In some embodiments, the distal flange is slidable along the protrusion and can travel through the opening until the distal flange comes into contact with the step of the protrusion. In some embodiments, the step can be positioned at a desired length L along the protrusion such that depression of the button face into the opening does not permit travel of the push button beyond a predetermined depth into the opening.

In some embodiments, the button face, distal face and sloped face form right angles with side faces of the push button, each of the side faces further comprising positioning tabs extending from the side faces and are substantially parallel to the button face. In some embodiments, the positioning tabs of the push button have a width which is greater than the width of the distal edge of the opening such that the push button cannot be removed from the opening.

In some embodiments, the device further comprises a cutter positioned over the proximal end of the plunger rod such that the cutter does not protrude beyond the open end, the cutter having a bottom surface and a top surface with the bottom surface abutting the proximal end of the plunger rod. In some embodiments, the cutter further comprises plurality of cut-outs positioned along the edge of the cutter, the plurality of cut-outs configured to interdigitate with a plurality of tabs positioned along the inside surface of the ejection compartment. In some embodiments, the cutter further comprises one or more of a central protrusion and an oval protrusion, the central protrusion and an oval protrusion configured to cut the seal. In some embodiments, the seal includes perforations and weak spots corresponding to one or more of the central protrusion and oval protrusion of the cutter.

In some embodiments, advancement of the push button in a medial direction by a finger of a single hand of a practitioner causes the sloped surface to bend the distal portion of the button retainer and the distal hook to advance in a proximal and medial direction, causing proximal advancement of the proximal end of the plunger rod. In some embodiments, proximal advancement of the proximal end of the plunger rod causes proximal advancement of a cutter which pierces the seal.

Further embodiments of the present disclosure are directed to a method of use of a hard package assembly with one-handed operation comprising the steps of depressing a button face of a push button by a finger of a practitioner, the push button positioned within an ejection compartment of a hard package container, pivoting a distal portion of a button retainer relative to a proximal portion of the button retainer such that a distal hook of the button retainer translates in a medial and proximal direction, advancing a barrel flange of a barrel of a syringe positioned within a main compartment of the hard package container by translation of the distal hook against a bottom surface of the barrel flange, advancing a plunger rod of the syringe in a proximal direction such that a proximal end of plunger rod pierces a seal, the seal covering an open end of the ejection compartment; and withdrawing the syringe from the hard package container.

In some embodiments, the method further comprises the steps of advancing the plunger rod abutting a cutter in a proximal direction.

Further embodiments of the present disclosure are directed to a method of assembly of a hard package assembly with one-handed operation comprising the steps of positioning a button retainer within an ejection compartment of a hard package container with guide tabs of the button retainer interdigitated with a retainer guide path of an inside surface of the ejection compartment, positioning a push button within the ejection compartment with a button face flush with an opening of the ejection compartment, and a sloped face of the push button abutting against a distal portion of the button retainer, positioning a barrel of a syringe having a plunger rod within a main compartment of the hard package container such that a bottom surface of a barrel flange is in contact with a distal hook of the button retainer, positioning a cutter over a proximal end of the plunger rod such that the cutter does not protrude beyond the open end of the ejection compartment and, covering the opening the open end with a seal.

Figure 1:
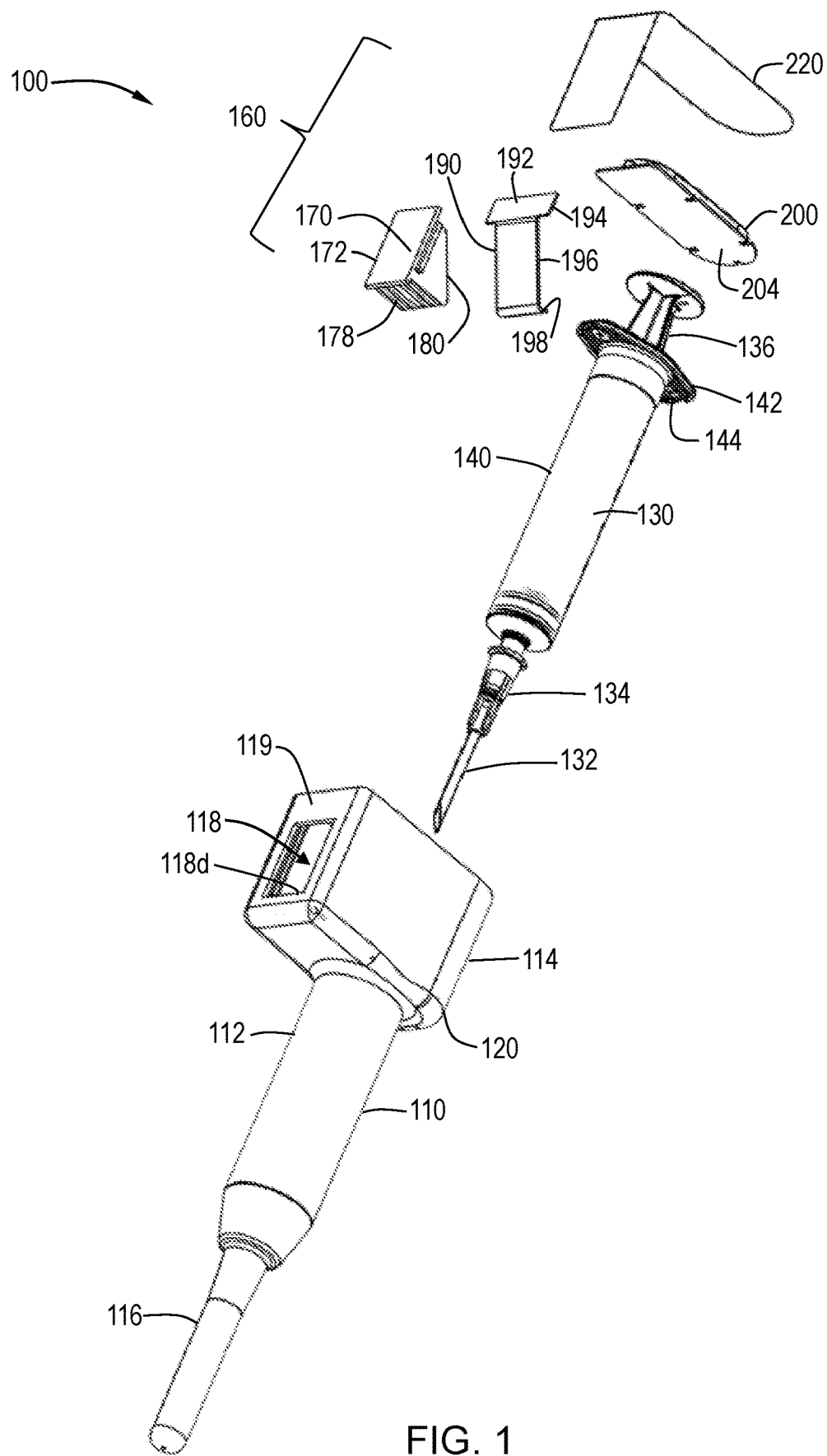
FIG. 1 illustrates an exploded view of a hard package assembly in accordance with one or more embodiments of the present disclosure.

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

In the appended figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label. The cross-hatch shading of the components in the figures are intended to aid in visualization of different parts and do not necessarily indicate different materials of construction.

DETAILED DESCRIPTION

Embodiments of the disclosure aims to provide a hard package for a syringe and cannula having a mechanism for single-hand opening and operation. In the embodiments described, the hard package implements a cam action for ejecting the syringe from the hard package while simultaneously piercing and opening a seal, allowing the syringe to protrude out from the hard package for ease of removal. The hard package in some embodiments can also be used for needle disposal by simply placing the needle and syringe back into the hard package.

Before describing several exemplary embodiments of the disclosure, it is to be understood that the disclosure is not limited to the details of construction or process steps set forth in the following description. The disclosure is capable of other embodiments and of being practiced or being carried out in various ways.

For purposes of the description hereinafter, the terms "top", "bottom", "longitudinal", and derivatives thereof shall relate to the disclosure as it is oriented in the drawing figures. However, it is to be understood that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

As used herein, the use of "a," "an," and "the" includes the singular and plural.

As used herein, the term "Luer connector" refers to a connection collar that is the standard way of attaching syringes, catheters, hubbed needles, IV tubes, etc. to each other. The Luer connector consists of one or more interlocking tubes, slightly tapered to hold together with just a simple pressure/twist fit/friction fit. Luer connectors can optionally include an additional outer rim of threading, allowing them to be more secure. The Luer connector can interlock and connect to the end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe. As used herein, the term "Luer connector" refers to a male luer connector or a female luer connector.

As used herein, the term "medical device" refers to common medical devices having threaded or interlocking connections, the connections having corresponding mating elements. By way of example but not limitation, a syringe may have a threaded connection which releasably interlocks with a secondary medical device such as a needless connector of a catheter, an IV line and the like. The threaded connection may include a lumen defining a fluid path surrounded by a protruding wall having the threaded means for attaching to the secondary medical device.

As would be readily appreciated by skilled artisans in the relevant art, while descriptive terms such as "thread", "taper", "tab", "wall", "top", "side", "bottom" and others are used throughout this specification to facilitate understanding, it is not intended to limit any components that can be used in combinations or individually to implement various aspects of the embodiments of the present disclosure.

As used herein, the terms "package" or "packaging" includes any material used to wrap or protect a good or product, such as a syringe or a needle. Packaging can be rigid or flexible. Packaging includes, but is not limited to, medical packaging, pharmaceutical packaging, and child-resistant packaging. Medical and pharmaceutical packaging can include hard packages.

As used herein, the term "hard package" or the like includes packaging having a compartment with one or more openings that can be covered to create a seal. In one or more embodiments, the hard package includes one or more components made of a rigid material such as a rigid polymeric material. Examples of rigid polymeric materials include, but are not limited to, polyester, polycarbonate, polyethylene, polystyrene or polypropylene, or combinations or co-polymers thereof. In one or more embodiments, a hard package can thermoformed or molded, such as by injection molding.

As used herein, the term "microorganism" refers to a microbe or organism that is unicellular or lives in a colony of cellular organisms. Microorganisms are very diverse; they include, but are not limited to bacteria, fungi, archaea, and protozoans.

Paramedics or emergency responders may have only one hand available to open packaging that was designed for two hands. This may force the practitioner to use of trauma shears and or teeth, which may cause contamination or delay treatment.

Figure 2:
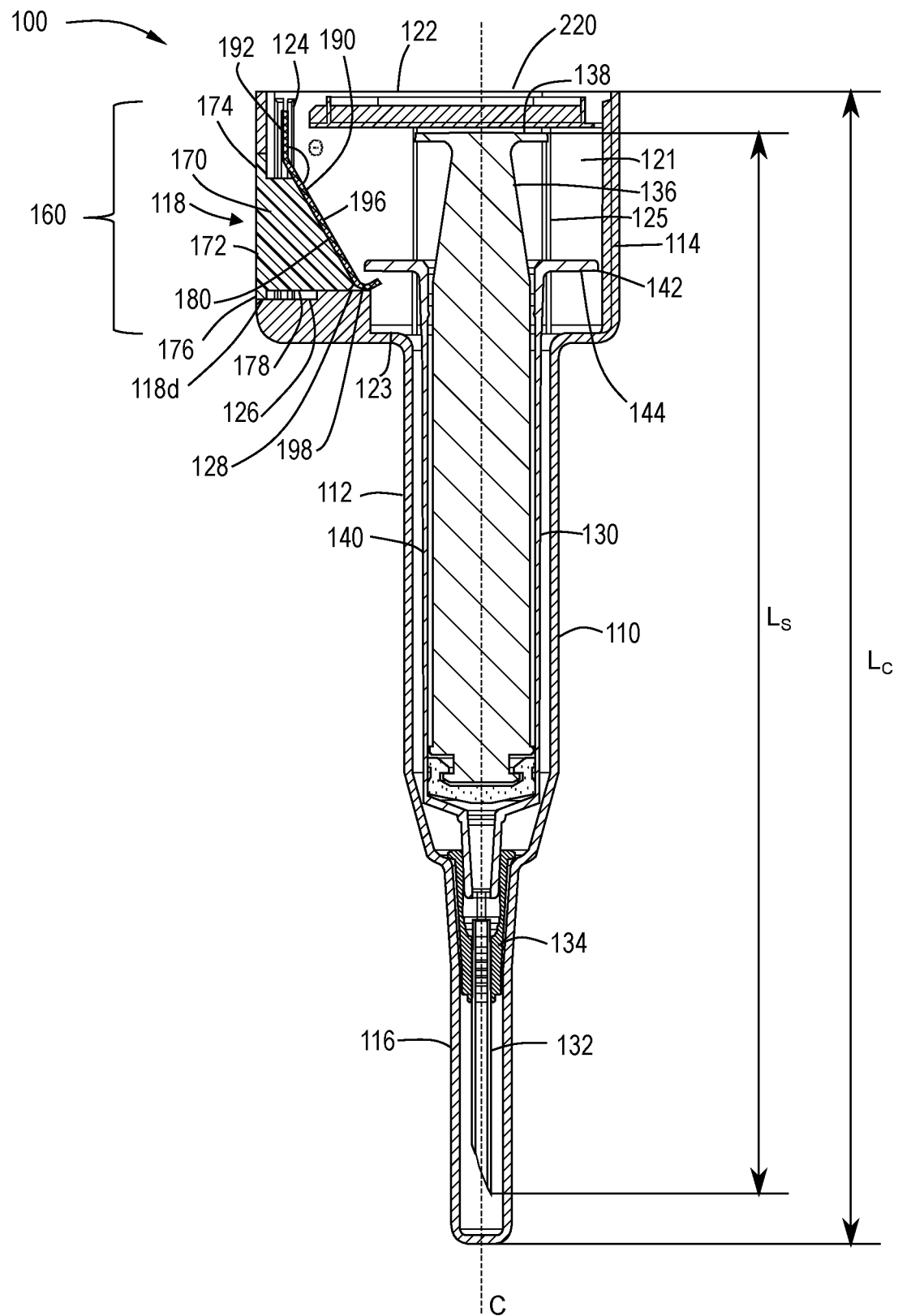
FIG. 2 illustrates a cross-sectional view of the hard package assembly in accordance with one or more embodiments of the present disclosure.

Embodiments of the present disclosure are directed to a hard package assembly 100 for storing a syringe 130. In the depicted embodiments, and as shown in FIGS. 1 and 2, the syringe 130 is a fill syringe 130 having a syringe barrel 140, a plunger rod 136, and a needle hub 134 and a needle cannula 132 connected to a luer connector of the barrel 140. In the depicted embodiment, the distal tip of the syringe has a Luer slip connector, however in other embodiments a needleless connector, threaded connector or other conventional means of connecting a syringe to a vascular access device can be utilized.

Referring now to the drawings, wherein like reference numerals designate identical or corresponding parts throughout the several views, embodiments of the present disclosure are described as follows. FIG. 1 illustrates an exploded view of the hard package assembly 100 and FIG. 2 illustrates a cross-sectional view of an assembled hard package assembly 100 in accordance with one or more embodiments. The hard package assembly 100 comprises a hard package container 110 in which a syringe 130 is positioned within. A cam mechanism 160 comprising a push button 170, a button retainer 190 and a cutter 200 are configured to pierce a seal 220 which encases the syringe 130 and the cam mechanism 160 within the container. As explained in further detail below, the cam mechanism 160 is also configured to eject the syringe 130 at least partially outside of the hard package container 110 such that a practitioner can pull the syringe 130 out with a one-handed operation and for immediate use in the field.

In the depicted embodiments, the syringe 130 includes the needle cannula 132 and needle hub 134, all of which are assembled and stored within the hard package container 110. In embodiments where the needle cannula 132 and needle hub 134 are not included, the hard package container 110 can be shorter overall to only accommodate the syringe 130. As shown in FIG. 2, the needle cannula 132 is stored without a cap, and in operation and use a practitioner can remove the syringe 130 and needle cannula 132 from the hard package container 110 without having to take the extra step to also remove a cap or protective sleeve of the needle cannula 132, however in some embodiments, the needle cannula 132 and needle hub 134 can include a cap for covering the needle cannula 132.

The hard package container 110 comprises a main compartment 112 and an ejection compartment 114, the ejection compartment 114 positioned proximally to the main compartment 112. In embodiments where the syringe 130 includes the needle cannula 132 and needle hub 134, the hard package container 110 further comprises a cannula compartment 116 distal to the syringe compartment for housing the needle cannula 132 and needle hub 134. The cannula compartment 116 configured as an inbuilt or integral needle shield for syringe activation and immediate and easy access to the syringe 130 and needle cannula 132.

The main compartment 112, ejection compartment 114 and cannula compartment 116 have a total hard package container length Lc equal to or slightly greater than a total length Ls of the syringe 130 (from a proximal end 138 of the plunger rod 136 to a tip of the needle cannula 132 of some embodiments). The main compartment 112 and cannula compartment 116 have a cylindrical shape. In some embodiments, one or more of the main compartment 112 and cannula compartment 116 are oval in shape for better single-hand grip and ergonomics. In some embodiments, one or more of the main compartment 112 and cannula compartment 116 are rectangular or square in shape. In embodiments where one or more of the main compartment 112 and cannula compartment 116 are non-cylindrical, longitudinal ribs positioned on the inside surface of the compartments can be configured to hold the contents within in place. The main compartment 112 and cannula compartment 116 share a common central axis C, and the ejection compartment 114 is offset from the central axis C.

As explained in further detail below, the barrel 140 is partially stored within the main compartment 112 and at least a barrel flange 142 of the barrel 140 is stored within the ejection compartment 114 along with the cam mechanism 160. As explained in further detail below, the button retainer 190 of the cam mechanism 160 is configured to push the syringe 130 out of the hard package container 110 in a proximal direction by pushing on a barrel flange 142 of the barrel 140. As the syringe 130 is advanced in a proximal direction, a proximal end 138 of the plunger rod 136 pushes against the cutter 200 in a proximal direction, the cutter 200 configured to pierce the seal 220.

Figure 3:
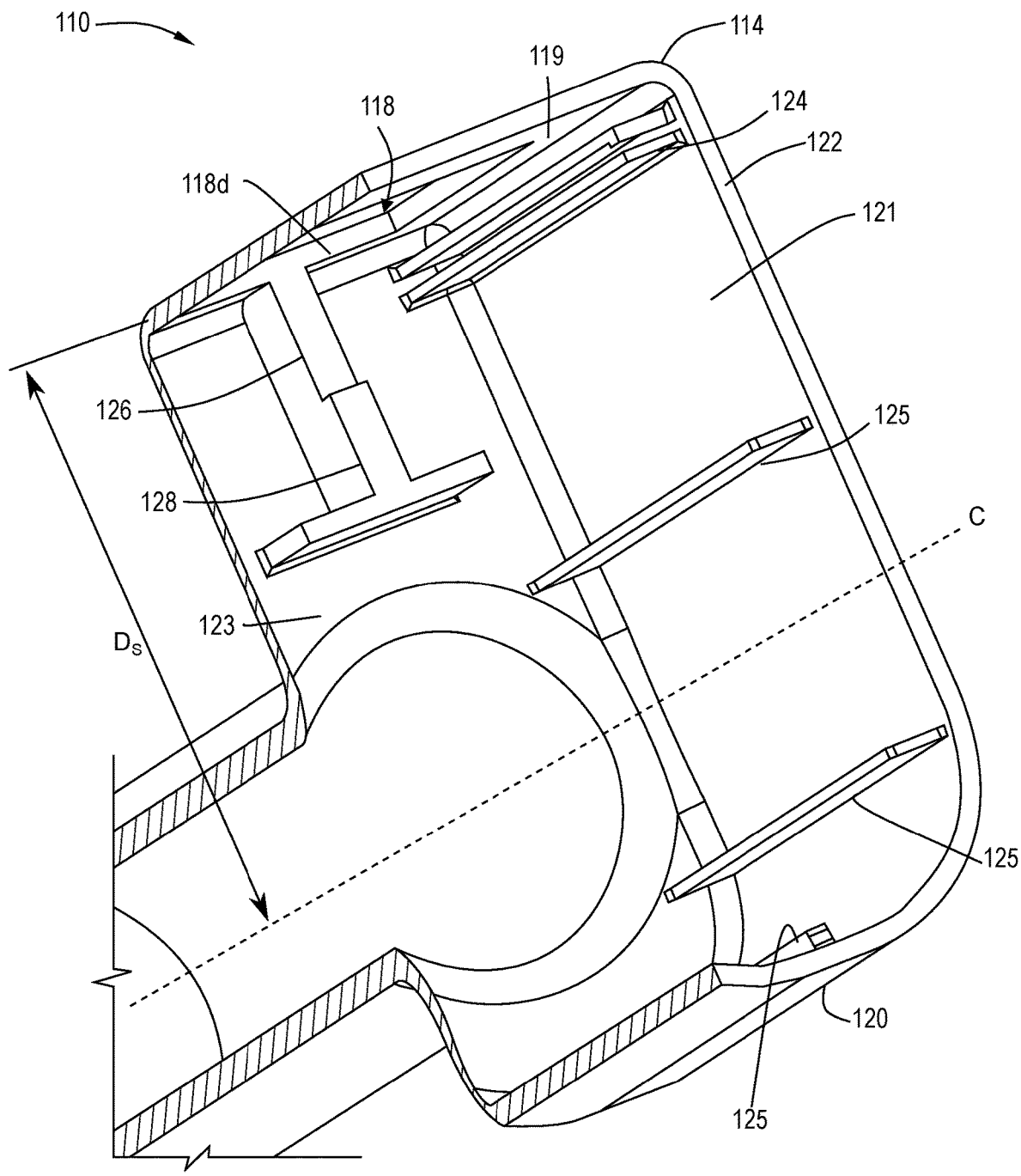
FIG. 3 illustrates a detailed cross-sectional view of the hard package assembly in accordance with one or more embodiments of the present disclosure.
Figure 4:
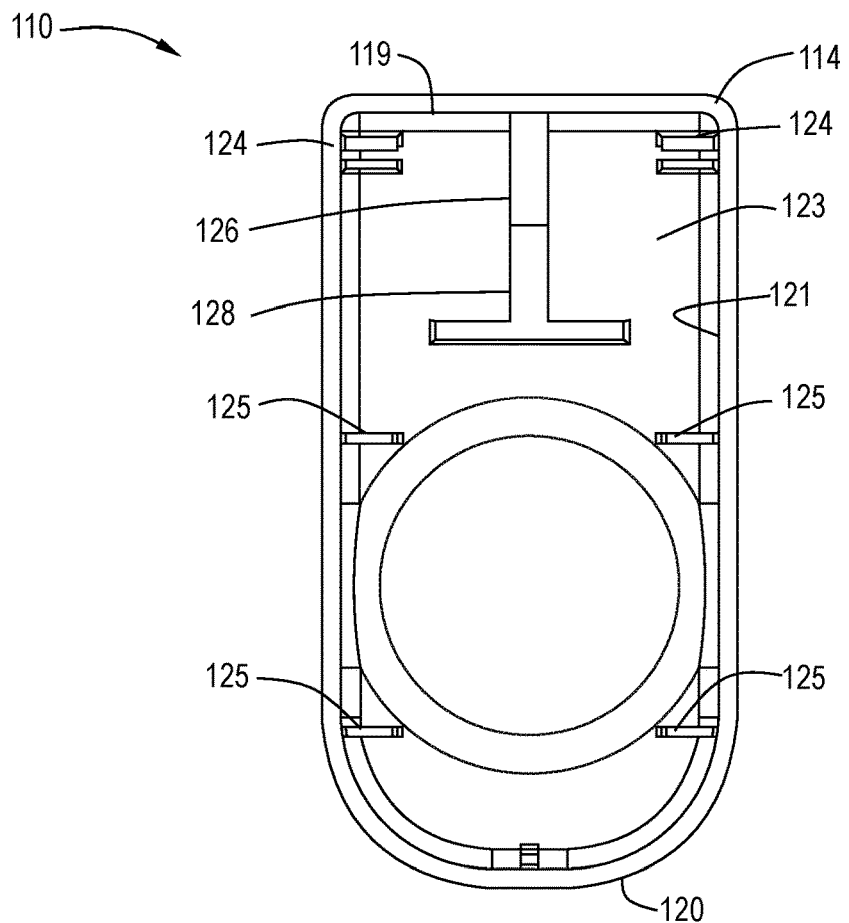
FIG. 4 illustrates a top view of the hard package assembly in accordance with one or more embodiments of the present disclosure.

Referring now to FIGS. 1 through 4, ejection compartment 114 of the hard package container 110 is described in further detail. FIG. 3 illustrates a cross-sectional view of the ejection compartment 114 and FIG. 4 illustrates a top view of the ejection compartment 114. In some embodiments, and as best shown in FIG. 4, the ejection compartment 114 has a rectangular cross-sectional shape with an opening 118 positioned on a short face 119 of the rectangular shape of the ejection compartment 114. In some embodiments, the ejection compartment 114 further comprises a rounded or oval face opposite the short face 119 for conforming to a hand of a practitioner.

As best shown in FIGS. 2 and 3, the ejection compartment 114 is offset from the central axis C, and the short face 119 extends a distance Ds from the central axis C such that components of the cam mechanism 160 can be positioned within the ejection compartment 114. The ejection compartment 114 is further defined by an inside surface 121, an open end 122 at a right angle and proximal to the short face 119 and a bottom surface 123 at a right angle and distal to the short face 119. Adjacent to the opening and positioned on the inside surface 121 is a retainer guide path 124 extending from the open end 122 towards the bottom surface 123. In some embodiments, the retainer guide path 124 is in the form of two protrusions extending from the inside surface 121 and configured to interdigitate with a guide tab 194 of the button retainer 190 as explained in further detail below. The retainer guide path 124 is configured to limit movement of the guide tab 194 of the button retainer 190 to only proximal-to-distal movement. The inside surface 121 further comprises a plurality of tabs 125 extending from the open end 122 towards the bottom surface 123. As explained in further detail below, the plurality of tabs 125 are configured to interdigitate with a plurality of cut-outs 206 of the cutter 200 such that the cutter 200 remains in position and can translate only within a distal-to-proximal direction.

The bottom surface 123 of the ejection compartment 114 comprises a protrusion 126 on which a distal face 178 of the push button 170 slides on as explained in further detail below. The protrusion 126 is adjacent to the opening 118 and extends from the bottom surface 123 in a proximal direction. The protrusion 126 of some embodiments does not extend beyond a distal edge 118d of the opening 118 such that the opening 118 is unobstructed. In some embodiments, the protrusion 126 further comprises a step 128 which extends beyond the distal edge 118d of the opening 118. As explained in further detail below, the step 128 is configured to limit travel of the push button 170 in a medial direction.

Figure 5:
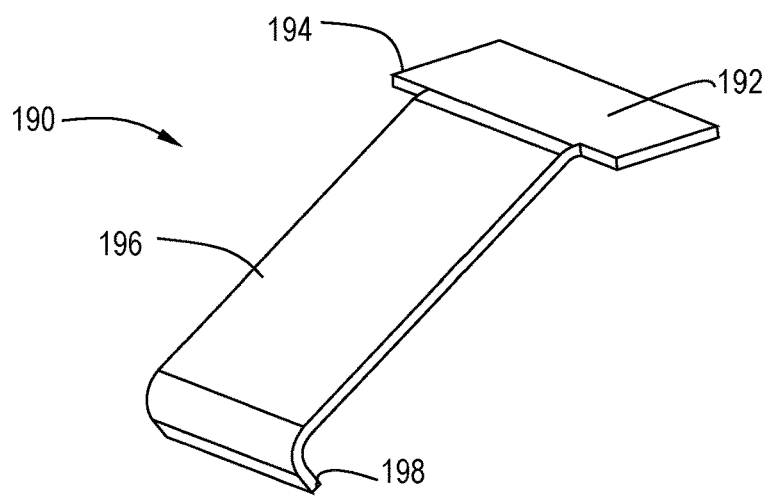
FIG. 5 illustrates a perspective view of a button retainer in accordance with one or more embodiments of the present disclosure.
Figure 6A:
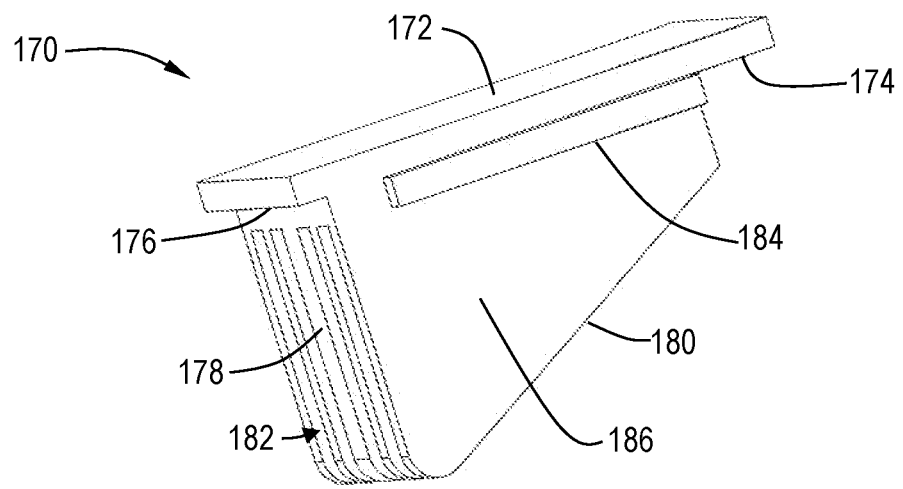
FIGS. 6A and 6B illustrate perspective views of a push button in accordance with one or more embodiments of the present disclosure.
Figure 6B:
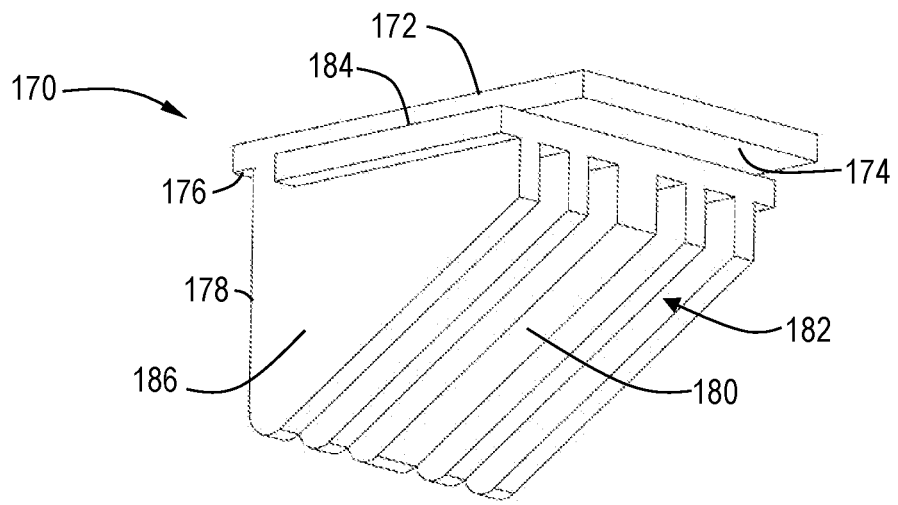

FIGS. 5 and 6A-6B illustrate components of the cam mechanism 160, with FIG. 5 illustrates the button retainer 190 and FIGS. 6A and 6B illustrate the push button 170. As shown in FIG. 5, the button retainer 190 comprises a proximal portion 192 and a distal portion 196. The button retainer 190 further comprises guide tabs 194 extending outwardly from the proximal portion 192. The distal portion 196 further comprises a distal hook 198 curving in a proximal direction relative to the distal portion 196. In some embodiments, the button retainer 190 is a leaf spring. In some embodiments, the button retainer 190 is spring steel. In some embodiments, as best shown in FIG. 2, the proximal portion 192 is at an angle Θ relative to the distal portion 196. In some embodiments, the button retainer 190 is configured to bend or flex between the proximal portion 192 and the distal portion 196 such that the angle θ decreases upon application of a medial force on the distal portion 196 as explained in further detail below.

As shown in FIGS. 6A and 6B, the push button 170 has a trapezoidal body having a button face 172, a distal face 178 adjacent and distal to the button face 172 and a sloped face 180 opposite the button face 172. In some embodiments, the button face further comprises a proximal flange 174 extending proximally from the button face 172 and a distal flange 176 extending distally from the button face 172. The button face 172, distal face 178 and sloped face 180 form right angles with side faces 186. Each of the side faces 186 in some embodiments further comprise positioning tabs 184 extending from the side faces 186 and are substantially parallel to the button face 172. As explained in further detail below, the proximal flange 174, distal flange 176, distal face 178 and positioning tabs 184 abut or slide against surfaces and features of the ejection compartment 114 to position and hold the push button 170 within the ejection compartment 114. In some embodiments, cut-outs 182 extend through the distal face 178 and the sloped face 180.

Figure 7:
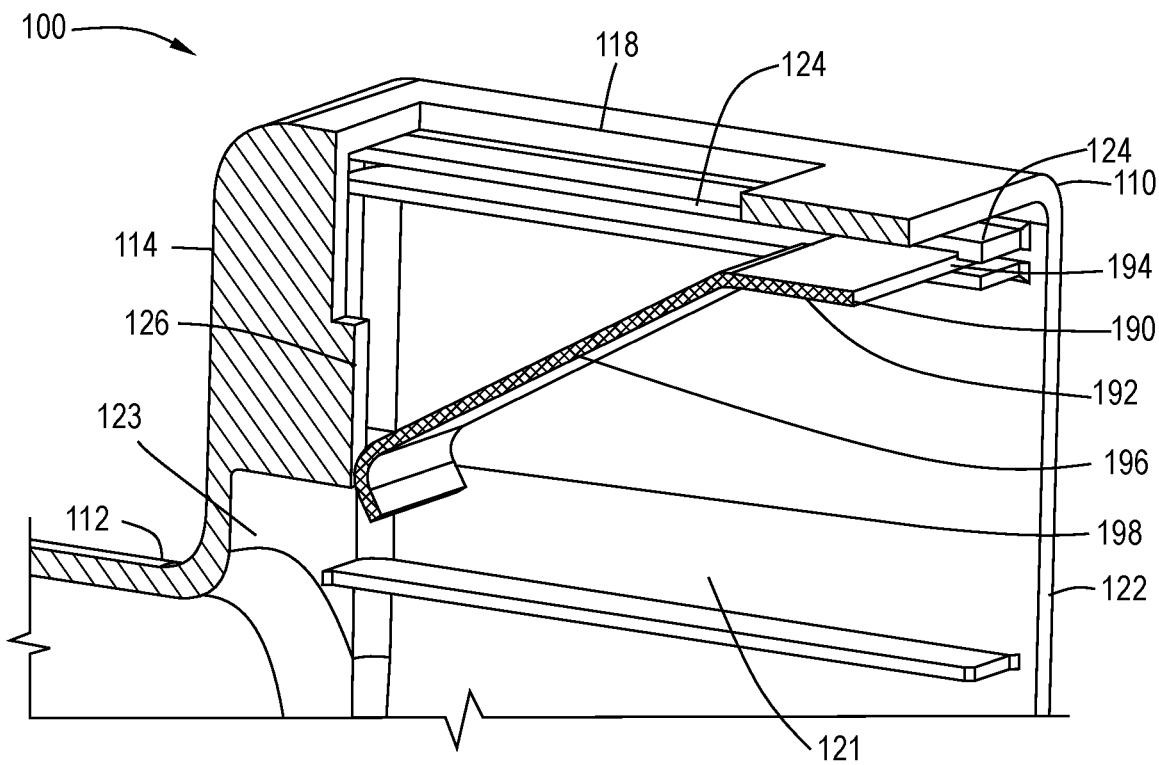
FIGS. 7 and 8 illustrate perspective cross-sectional views of the hard package assembly in accordance with one or more embodiments of the present disclosure.
Figure 8:
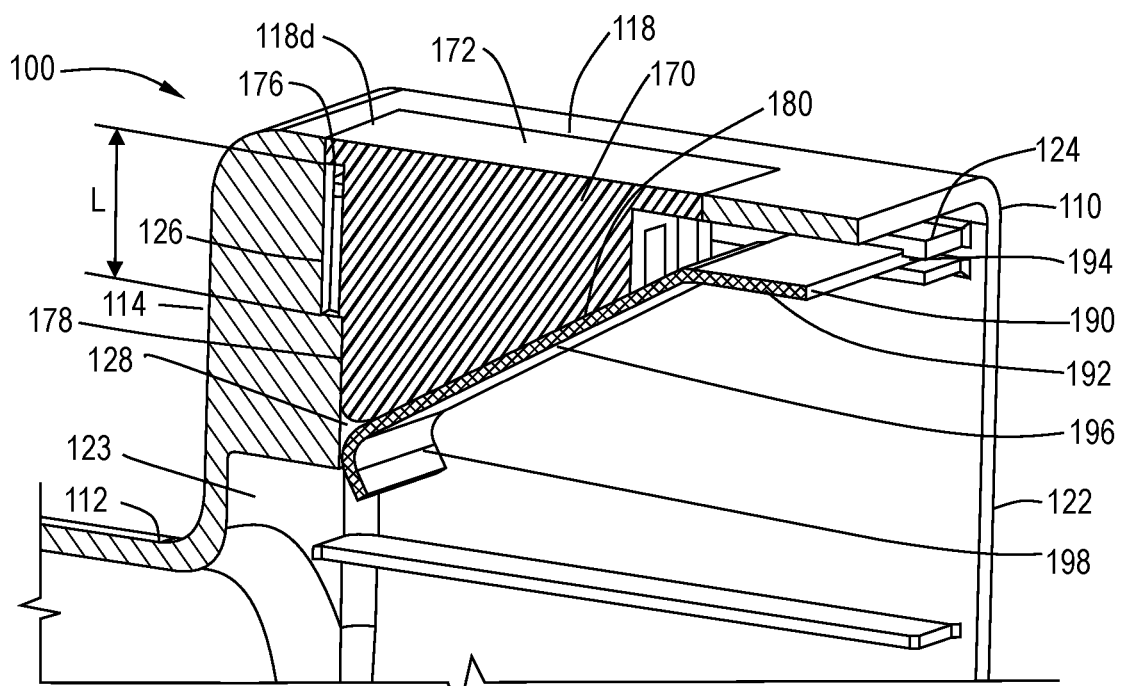
Figure 9:
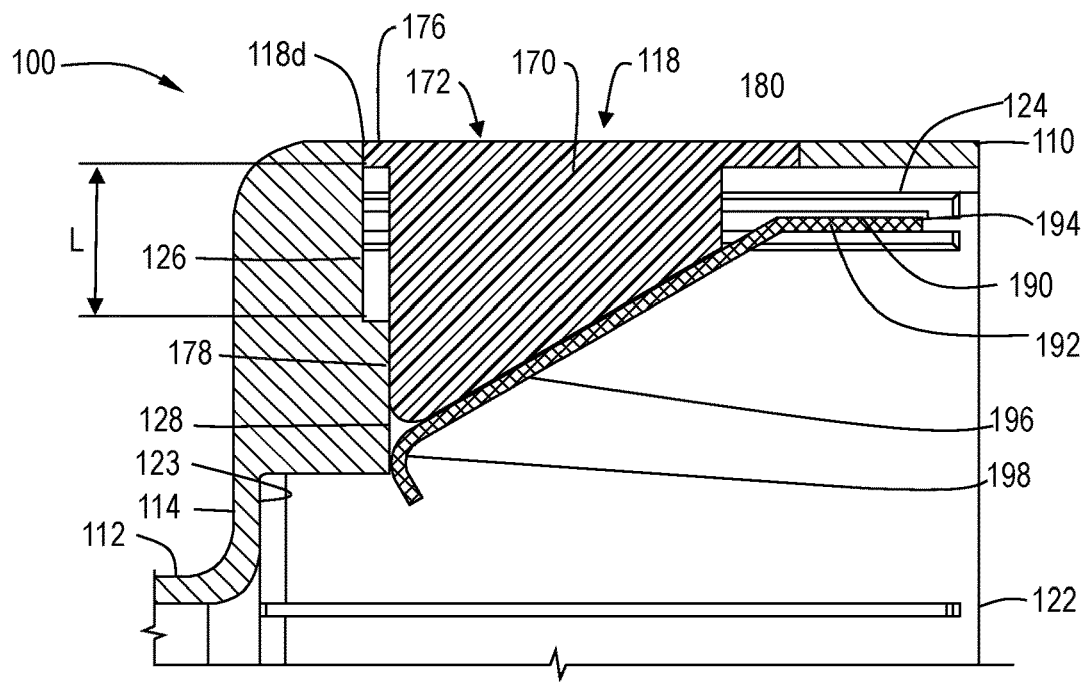
FIG. 9 illustrates a side cross-sectional view of the hard package assembly in accordance with one or more embodiments of the present disclosure.
Figure 10:
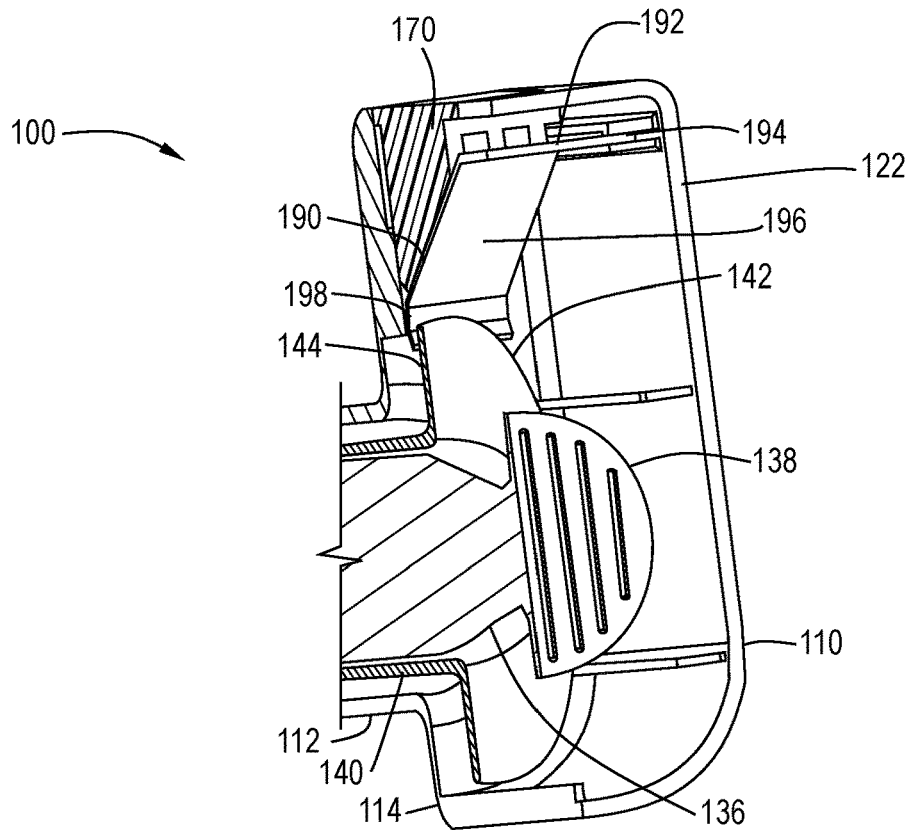
FIG. 10 illustrates perspective cross-sectional view of the hard package assembly in accordance with one or more embodiments of the present disclosure.
Figure 11:
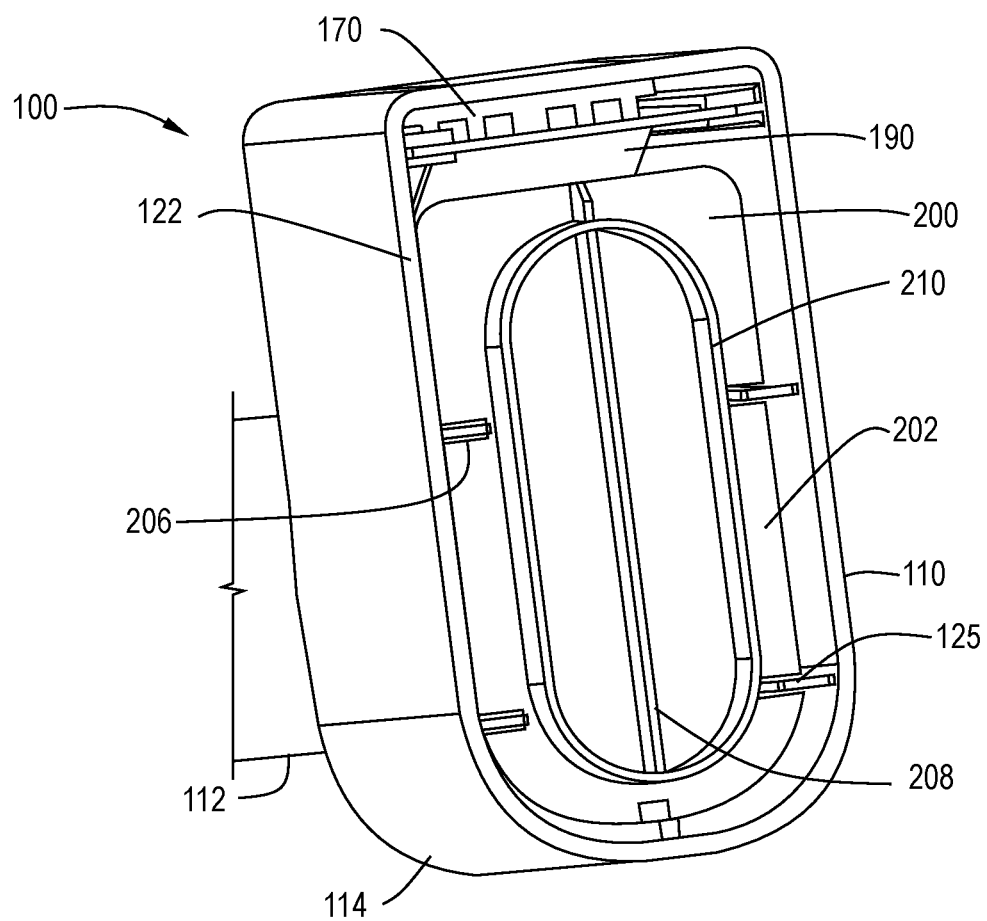
FIG. 11 illustrates perspective view of the hard package assembly in accordance with one or more embodiments of the present disclosure; and, FIGS. 12 and 13 illustrates perspective cross-sectional views of the hard package assembly in accordance with one or more embodiments of the present disclosure.

FIGS. 7-11 illustrate the cam mechanism 160 of one or more of the previously described embodiments positioned within the ejection compartment 114 along with the syringe 130. FIG. 7 illustrates the button retainer 190 first positioned within the ejection compartment 114, and FIGS. 8 and 9 illustrate the push button 170 then positioned within the ejection compartment 114. As shown in FIG. 10, the syringe 130 is then positioned within the ejection compartment 114 and the cutter 200 is placed over the syringe 130 as shown in FIG. 11. The seal 220 is then placed over the opening 118 and the open end 122 of the ejection compartment 114 sealing the contents within, as shown in FIGS. 1, 2, 12 and 13.

As shown in FIG. 7, the button retainer 190 is first positioned within the ejection compartment 114 with the guide tabs 194 of the button retainer 190 interdigitated with the retainer guide path 124 of the inside surface 121 of the ejection compartment 114. It is to be understood that FIG. 7 illustrates a cross-section of the ejection compartment 114 and the retainer guide path 124 is on both and opposite sides of the inside surface 121. Likewise, as previously shown in FIG. 5, guide tabs 194 extend from opposite sides of the proximal portion 192 of the button retainer 190. The guide tabs 194, the proximal portion 192 and the retainer guide path 124 are parallel to the opening 118. As such, the distal portion 196 of the button retainer 190 extends inwardly in a medial direction due to the angle θ of the proximal portion 192 relative to the distal portion 196. As previously explained, the distal hook 198 curves in a proximal direction toward the opening 118. In some embodiments, the distal hook 198 is in contact with the protrusion 126 of the bottom surface 123 of the compartment. In some embodiments, the distal hook 198 is free-standing with the button retainer 190 held within the ejection compartment 114 only by the retainer guide path 124.

As shown in FIGS. 7 and 8, the push button 170 is positioned within the ejection compartment 114 with the button face 172 flush with the opening 118. The button face 172, proximal flange 174 and distal flange 176 substantially cover the opening 118 with the button face 172 having a width less than a width of the opening 118, and the distal flange 176 abutting the distal edge 118d. The distal face 178 abuts and is slidable along the step 128 of the protrusion 126. In some embodiments, the distal face 178 can travel through the opening 118 until the distal flange 176 comes into contact with the step 128 of the protrusion 126. Thus, the step 128 can be positioned at a desired length L along the protrusion 126 such that depression of the button face 172 into the opening 118 does not permit travel of the push button 170 travel beyond a predetermined depth into the opening 118.

As shown, the sloped face 180 of the push button 170 of some embodiments abuts against the distal portion 196 of the button retainer 190. Due to the guide tabs 194 of the proximal portion 192 of the button retainer 190 limiting the movement of the proximal portion 192 of the button retainer 190, depression of the button face 172 into the opening 118 pushes against the distal portion 196 of the button retainer 190, causing the distal portion 196 to pivot relative to the proximal portion 192, thereby pushing the distal portion 196 and distal hook 198 in a medial and proximal direction relative to the proximal portion 192.

The positioning tabs 184 of the push button 170 have a width (from a positioning tab 184 of one side face 186 to a positioning tab 184 of the opposite side face 186) which is greater than the width of the distal edge 118d of the opening 118 such that the push button 170 cannot be removed from the opening due to the positioning tab 184 being wider than the opening 118.

As shown in FIG. 10, the barrel 140 is positioned within the main compartment 112 such that the bottom surface 144 of the barrel flange 142 is in contact with the distal hook 198 of the button retainer 190 with the proximal end 138 of plunger rod 136 not protruding beyond the open end 122. As previously stated, depression of the button face 172 into the opening 118 pushes against the distal portion 196 of the button retainer 190, causing the distal portion 196 to pivot relative to the proximal portion 192, thereby pushing the distal portion 196 and distal hook 198 in a medial and proximal direction relative to the proximal portion 192. The distal hook 198 pushes the bottom surface 144 of the barrel flange 142 and the proximal end 138 of plunger rod 136 in a proximal direction with at least the proximal end 138 of plunger rod 136 protruding past the open end 122.

As shown in FIG. 11, the cutter 200 is positioned over the proximal end 138 of plunger rod 136 such that the cutter 200 does not protrude beyond the open end 122. The cutter 200 comprises a top surface 202 and a bottom surface 204 with the bottom surface 204 abutting the proximal end 138 of plunger rod 136. The cutter 200 further comprises a plurality of cut-outs 206 positioned along the edge of the cutter 200. The cut-outs 206 are configured to interdigitate with the plurality of tabs 125 of the inside surface 121 such that the cutter 200 remains in position and can translate only within a distal-to-proximal direction. The top surface 202 comprises one or more of a central protrusion 208 and an oval protrusion 210 which can correspond to weak points of the seal 220. In some embodiments, one or more of a central protrusion 208 and an oval protrusion 210 can be sharp. In some embodiments, one or more of a central protrusion 208 and an oval protrusion 210 protrude beyond the other.

As previously stated, in some embodiments the button face 172 is limited in medial travel by the length L due to the distal flange 176 abutting against the step 128 of the protrusion 126. The length L in some embodiments can be configured to cause a desired and limited proximal translation of the distal portion 196 and distal hook 198 as the distal portion 196 pivots relative to the proximal portion 192 of the button retainer 190. Thus, in some embodiments the length L can be limited to reduce travel or activation distance of the push button 170, button retainer 190, barrel flange 142, proximal end 138 of plunger rod 136 and cutter 200 such that the cutter 200 breaks beyond the seal 220 and the proximal end 138 of plunger rod 136 protrudes sufficiently outside of the open end 122 for a practitioner to grasp the plunger rod 136.

Figure 12:
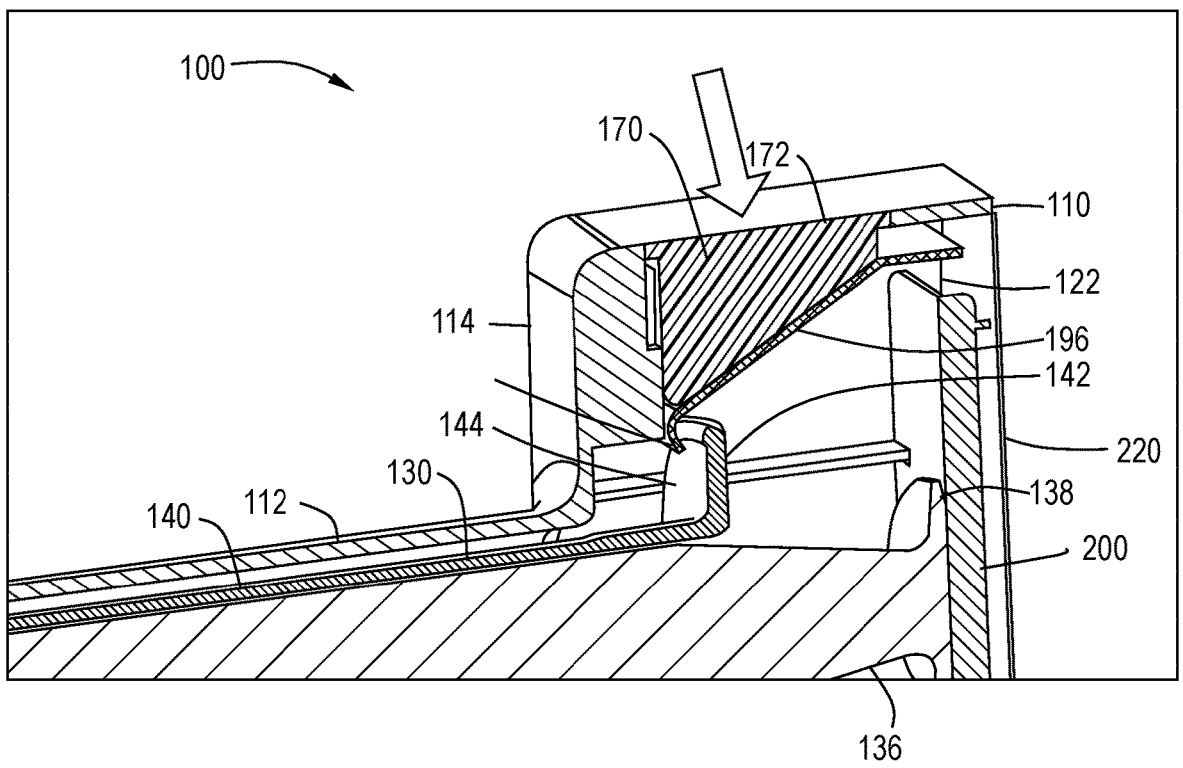
Figure 13:
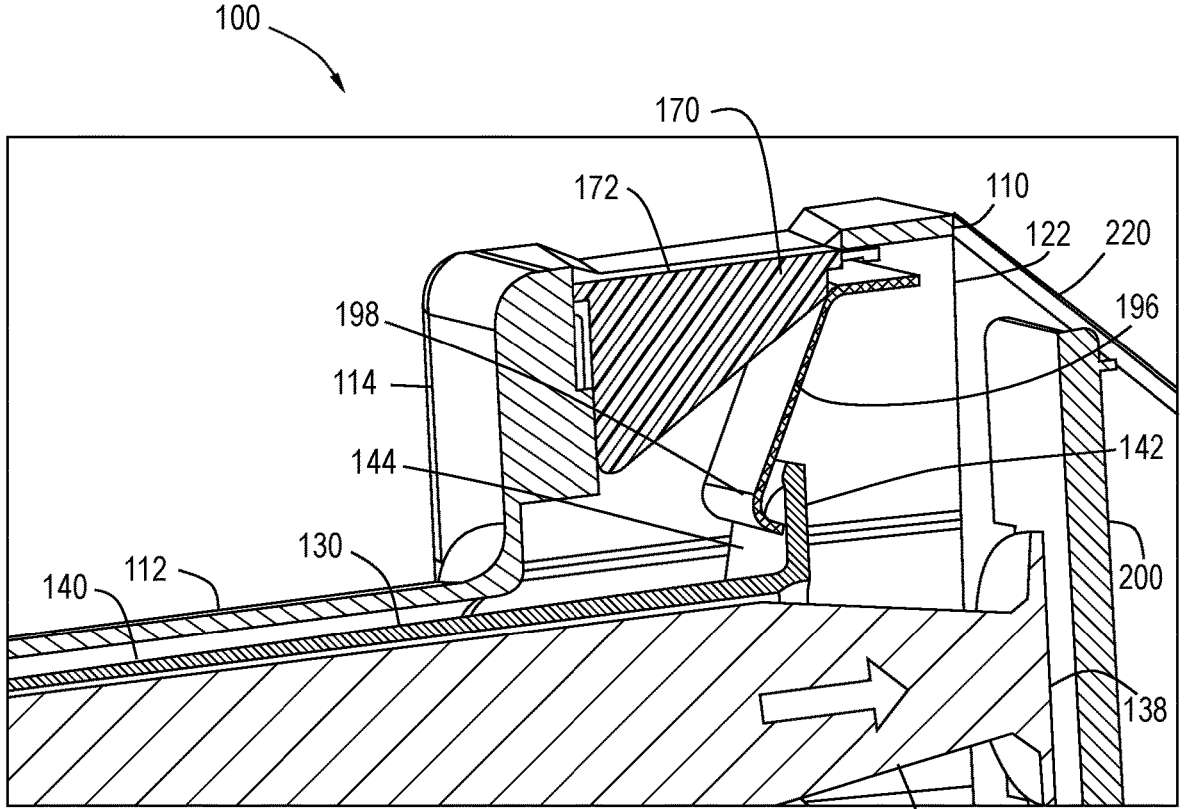

As shown in FIGS. 12 and 13, the seal 220 covers and seals the opening 118 and the open end 122 of the ejection compartment 114. In some embodiments, two different seals 220 cover each of the opening 118 and the open end 122 of the ejection compartment 114. In some embodiments, one seal 220 covers each of the opening 118 and the open end 122 of the ejection compartment 114. The seal 220 covering the opening 118 can have perforations or weak points such that a finger of a practitioner can puncture the button face 172 of the push button 170. Likewise, the seal 220 covering the open end 122 can have perforations or weak points such that the cutter 200 can pierce the seal 220. In an alternative embodiment of the hard package assembly 100, the cutter 200 is omitted and the seal 220 covering the open end 122 can have perforations or weak points corresponding to the proximal end 138 of plunger rod 136 such that the proximal end 138 of plunger rod 136 can pierce the seal 220. The hard package assembly 100, fully sealed by the seal 220 can undergo ETO sterilization.

FIGS. 12 and 13 illustrate a method of use of the hard package assembly 100 with one-handed operation. The method comprises the steps of depressing the button face 172 of the push button 170 by a finger of a practitioner. Pivoting the distal portion 196 of the button retainer 190 relative to the proximal portion 192 of the button retainer 190 such that the distal hook 198 translates in a medial and proximal direction. Advancing the barrel flange 142 of the barrel 140 by translation of the distal hook 198 against the bottom surface 144 of the barrel flange 142. In some embodiments, advancing the plunger rod 136 in a proximal direction such that the proximal end 138 of plunger rod 136 pierces the seal 220. In some embodiments, advancing the plunger rod 136 abutting the cutter 200 in a proximal direction such that the cutter 200 pierces the seal 220. The plunger rod 136 is advanced out from the open end 122 a sufficient distance to be grasped by two fingers of one hand. In some embodiments, the method further comprises the steps of depressing the button face 172 of the push button 170 by an index finger of one hand and subsequently grasping the plunger rod 136 with the index finger and thumb of one hand as the hard package assembly 100 is permitted to fall out of the hand and palm of the hand, thereby allowing for free manipulation and gripping of the syringe 130 by one hand.

FIGS. 7-12 illustrate a method of assembly of the hard package assembly 100. The method comprises the steps of positioning the button retainer 190 is within the ejection compartment 114 with the guide tabs 194 of the button retainer 190 interdigitated with the retainer guide path 124 of the inside surface 121 of the ejection compartment 114. Positioning the push button 170 within the ejection compartment 114 with the button face 172 flush with the opening 118 and the sloped face 180 of the push button 170 abutting against the distal portion 196 of the button retainer 190. Positioning the barrel 140 is within the main compartment 112 such that the bottom surface 144 of the barrel flange 142 is in contact with the distal hook 198 of the button retainer 190 with the proximal end 138 of plunger rod 136 not protruding beyond the open end 122. In some embodiments, positioning the cutter 200 over the proximal end 138 of plunger rod 136 such that the cutter 200 does not protrude beyond the open end 122. Covering the opening 118 and the open end 122 with a seal 220.

In some embodiments, the main compartment 112, ejection compartment 114 and cannula compartment 116 are translucent and see-through. In some embodiments, the seal 220 comprises MGP paper. In some embodiments, the seal 220 includes instructions or indications printed on the seal 220. In some embodiments, the seal 220 includes a symbol indicating to push the push button 170. In some embodiments, the seal 220 can have depressions following cutter profiles of the cutter 200 for quick tearing of the seal 220. By way of example but not limitation, the seal 220 can have weak points or depressions which match the central protrusion 208 and oval protrusion 210 of the cutter 200. In some embodiments, the main compartment 112, ejection compartment 114, cannula compartment 116, push button 170 and cutter 200 are polypropylene or Yuplene R370Y resin. In some embodiments, the main compartment 112, ejection compartment 114 and cannula compartment 116 are a single, injection molded unitary body. In some embodiments, the push button 170 is injection molded.

In some embodiments, the hard package assembly 100 is activated by pressing the button face 172 of the push button 170. In some embodiments, the resistance of the button retainer 190 is configured to bend under normal forces exerted by the thumb of a practitioner gripping the ejection compartment 114 and the oval face 120 in one hand. In other embodiments, the resistance can be lesser to include single-hand operation use with other fingers such as the index finger. In some embodiments, the hard package assembly 100 is held in one hand vertically or horizontally. Thus, due to the hard package assembly 100 being operated with one hand, and with a variety of fingers and orientations, the hard package assembly 100 can be used quickly in emergency conditions. Thus, better time, safety and space efficiency is achieved, even in emergency situation at the emergency site.

In some embodiments, it is contemplated that automatic line packaging methods, including kit packing and robotic handling may be utilized.

While the present disclosure has been shown and described with reference to certain exemplary embodiments thereof, it will be understood by those skilled in the art that various changes in form and details may be made therein without departing from the spirit and scope of the embodiments of the present disclosure. Also, the inner and/or the outer housing of the disinfection cap can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to limit the scope or content of the inventive design or methodology as understood by artisans skilled in the relevant technical field.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A single-hand operable assembly comprising:
a hard package container comprising a main compartment and an ejection compartment, the ejection compartment having a rectangular cross-sectional shape with an opening having a distal edge positioned on a short face of the rectangular shape of the ejection compartment, the ejection compartment having an inside surface, an open end at a right angle and proximal to the short face and a bottom surface at a right angle and distal to the short face;
a syringe having a plunger rod and a barrel positioned at least partially within the main compartment, the plunger rod having a proximal end, the barrel having a barrel flange, the barrel flange having a bottom surface;
a cam mechanism comprising a push button and a button retainer, the push button having a trapezoidal body having a button face, a distal face adjacent and distal to the button face and a sloped face opposite the button face, the button retainer having a proximal portion, a distal portion in contact with the sloped face of the push button and a distal hook in contact with a bottom surface of the barrel flange; and,
a seal covering the open end and the button face.

2. The assembly of claim 1, wherein the syringe further comprising a needle hub and needle cannula, the needle hub and needle cannula stored without a needle cap or sleeve within a cannula compartment of the hard package container.

3. The assembly of claim 2, wherein the main compartment and cannula compartment share a common central axis C.

4. The assembly of claim 1, wherein the main compartment has a central axis C and the ejection compartment is offset from the central axis C, and the short face extends a distance Ds from the central axis C such that components of the cam mechanism can be positioned within the ejection compartment.

5. The assembly of claim 1, wherein the ejection compartment further comprises a rounded or oval face opposite the short face for conforming to a hand of a practitioner.

6. The assembly of claim 1, the ejection compartment further comprising a retainer guide path adjacent to the opening and positioned on the inside surface of the ejection compartment, the retainer guide path configured to interdigitate with a guide tab of the button retainer.

7. The assembly of claim 6, wherein the retainer guide path has of two protrusions extending from the inside surface of the ejection compartment.

8. The assembly of claim 1, wherein the button retainer further comprises guide tabs extending outwardly from the proximal portion, the guide tabs configured to interdigitate with retainer guide path adjacent to the opening and positioned on the inside surface of the ejection compartment, the guide tabs configured to allow pivoting of the distal portion relative to the proximal portion.

9. The assembly of claim 1, wherein the bottom surface of the ejection compartment further comprises a protrusion on which the distal face of the push button slides on, the protrusion adjacent to the opening and extends from the bottom surface in a proximal direction.

10. The assembly of claim 9, wherein the protrusion does not extend beyond the distal edge of the opening such that the opening is unobstructed.

11. The assembly of claim 9, the protrusion further comprises a step which extends beyond the distal edge of the opening, the step configured to limit travel of the push button in a medial direction.

12. The assembly of claim 11, the push button further comprising a distal flange extending distally from the button face, the distal flange abutting the distal edge of the opening, the distal flange slidable along the protrusion of the bottom surface.

13. The assembly of claim 12, wherein the distal flange is slidable along the protrusion and can travel through the opening until the distal flange comes into contact with the step of the protrusion.

14. The assembly of claim 11, wherein the step can be positioned at a desired length L along the protrusion such that depression of the button face into the opening does not permit travel of the push button beyond a predetermined depth into the opening.

15. The assembly of claim 1, wherein the button face, distal face and sloped face form right angles with side faces of the push button, each of the side faces further comprising positioning tabs extending from the side faces and are substantially parallel to the button face.

16. The assembly of claim 15, wherein positioning tabs of the push button have a width which is greater than the width of the distal edge of the opening such that the push button cannot be removed from the opening.

17. The assembly of claim 1 further comprising a cutter positioned over the proximal end of the plunger rod such that the cutter does not protrude beyond the open end, the cutter having a bottom surface and a top surface with the bottom surface abutting the proximal end of the plunger rod.

18. The assembly of claim 17, wherein the cutter further comprises plurality of cut-outs positioned along the edge of the cutter, the plurality of cut-outs configured to interdigitate with a plurality of tabs positioned along the inside surface of the ejection compartment.

19. The assembly of claim 17, wherein the cutter further comprises one or more of a central protrusion and an oval protrusion, the central protrusion and an oval protrusion configured to cut the seal.

20. The assembly of claim 19, wherein the seal includes perforations and weak spots corresponding to one or more of the central protrusion and oval protrusion of the cutter.

21. The assembly of claim 1, wherein advancement of the push button in a medial direction by a finger of a single hand of a practitioner causes the sloped surface to bend the distal portion of the button retainer and the distal hook to advance in a proximal and medial direction, causing proximal advancement of the proximal end of the plunger rod.

22. The assembly of claim 21, wherein proximal advancement of the proximal end of the plunger rod causes proximal advancement of a cutter which pierces the seal.

23. A method of use of a hard package assembly with one-handed operation comprising the steps of:
depressing a button face of a push button by a finger of a practitioner, the push button positioned within an ejection compartment of a hard package container;
pivoting a distal portion of a button retainer relative to a proximal portion of the button retainer such that a distal hook of the button retainer translates in a medial and proximal direction;

advancing a barrel flange of a barrel of a syringe positioned within a main compartment of the hard package container by translation of the distal hook against a bottom surface of the barrel flange;

advancing a plunger rod of the syringe in a proximal direction such that a proximal end of plunger rod pierces a seal, the seal covering an open end of the ejection compartment; and, withdrawing the syringe from the hard package container.

24. The method of claim 23 further comprising the steps of advancing the plunger rod abutting a cutter in a proximal direction.

25. A method of assembly of a hard package assembly with one-handed operation comprising the steps of:

positioning a button retainer within an ejection compartment of a hard package container with guide tabs of the button retainer interdigitated with a retainer guide path of an inside surface of the ejection compartment;

positioning a push button within the ejection compartment with a button face flush with an opening of the ejection compartment, and a sloped face of the push button abutting against a distal portion of the button retainer;

positioning a barrel of a syringe having a plunger rod within a main compartment of the hard package container such that a bottom surface of a barrel flange is in contact with a distal hook of the button retainer;

positioning a cutter over a proximal end of the plunger rod such that the cutter does not protrude beyond the open end of the ejection compartment; and, covering the opening of the open end with a seal.

* * * * *